(12) United States Patent
Horbaschek et al.

(10) Patent No.: US 6,370,417 B1
(45) Date of Patent: Apr. 9, 2002

(54) METHOD FOR POSITIONING A CATHETER IN A VESSEL, AND DEVICE FOR IMPLEMENTING THE METHOD

(75) Inventors: Heinz Horbaschek; Johann Seissl, both of Erlangen (DE); Ali-Reza Bani-Hashemi, Walnut Creek, CA (US)

(73) Assignee: Siemens Akiengesellschaft, Munich (DE)

( * ) Notice: Subject to any disclaimer, the term of this patent is extended or adjusted under 35 U.S.C. 154(b) by 0 days.

(21) Appl. No.: 09/401,448

(22) Filed: Sep. 22, 1999

(30) Foreign Application Priority Data

Sep. 22, 1998 (DE) .......................................... 198 43 408

(51) Int. Cl.$^7$ ................................................ A61B 5/05
(52) U.S. Cl. ........................ 600/424; 600/425; 600/431; 600/433; 600/434; 382/128; 378/4; 378/7; 378/9; 378/20; 378/21; 378/62
(58) Field of Search ................................ 600/407, 410, 600/411, 417, 429, 431, 433, 436, 437, 458; 378/4, 6, 19, 21, 42, 44, 46; 382/128, 131, 132, 154, 284, 285; 250/370.09

(56) References Cited

U.S. PATENT DOCUMENTS

| 4,709,385 A | | 11/1987 | Pfeiller et al. |
| 5,588,033 A | * | 12/1996 | Yeung ............................. 378/4 |
| 5,713,946 A | | 2/1998 | Ben-Haim |
| 5,810,728 A | * | 9/1998 | Kuhn .......................... 600/410 |
| 6,019,725 A | * | 2/2000 | Vesely et al. ................ 600/447 |

FOREIGN PATENT DOCUMENTS

DE 42 25 112 12/1993

\* cited by examiner

*Primary Examiner*—Marvin M. Lateef
*Assistant Examiner*—Jeoyuh Lin
(74) *Attorney, Agent, or Firm*—Schiff Hardin & Waite

(57) ABSTRACT

In a method for positioning a catheter that has been inserted into a vessel and a device for implementing the method, the road map technique is used, wherein as a mask image, a three-dimensional mask image of the vessel which is composed of number of individual mask images is employed. From these individual mask images, that individual mask image is selected whose exposure direction corresponds optimally to the exposure direction of an instantaneously captured individual image, in order to combine this selected individual mask image with the instantaneously captured mask image and to display the resulting combined image.

20 Claims, 2 Drawing Sheets

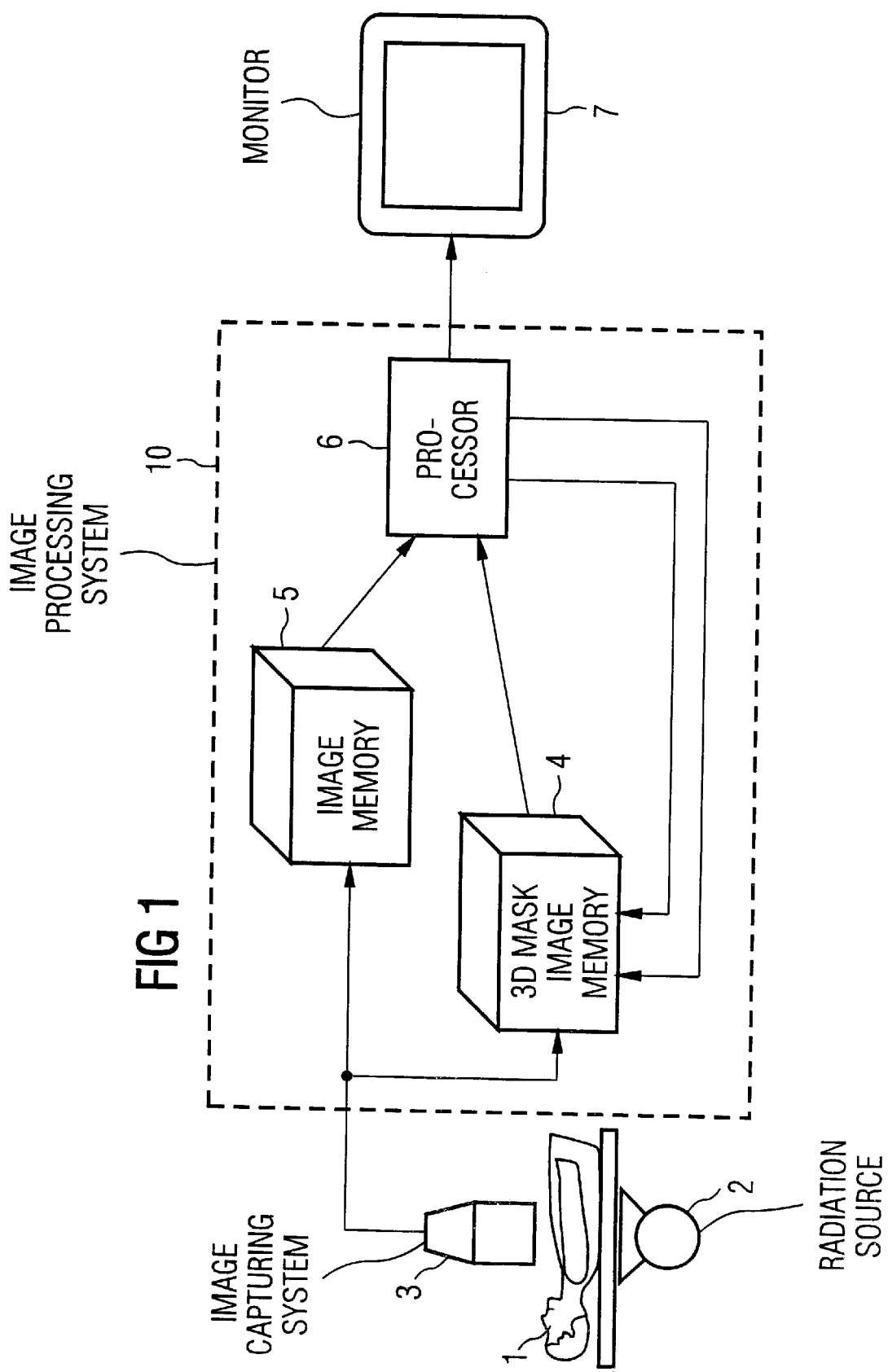

METHOD FOR POSITIONING A CATHETER IN A VESSEL, AND DEVICE FOR IMPLEMENTING THE METHOD

BACKGROUND OF THE INVENTION

1. Field of the Invention

The present invention is directed to a method for positioning a catheter that has been inserted into a vessel and to a device for implementing the method, the device being particularly for conducting an angiographic examination of a subject.

2. Description of the Prior Art

In angiographic examinations, i.e. in radiological examinations of blood vessels or lymphatic vessels, a catheter is inserted into the examined vessel, by means of which a specific contrast agent can be injected into the vessel in order to improve the contrast of the captured X-ray image at the examined location, the corresponding vessel being brought into prominence in the X-ray image by the contrast agent injection. For this purpose the catheter must first be led to the respective target location, i.e. to the desired examination location. The positioning of the catheter in angiographic examinations thus has a special significance, since what is particularly important in the positioning of the catheter to follow the branchings of the vessel accurately and to reach the desired target location (where there is a stenosis or an aneurism [sic], for example) precisely and without interruption.

For this reason, a technique known as the road map technique (pathfinder technique) has long been used, which facilitates positioning of the catheter in a vessel that is to be examined. In this technique, a small amount of contrast agent is injected into the vessel via the catheter while transirradiating the vessel, and, as soon as the vessel gives an image, the transirradiation is interrupted and the last radiographic image is stored as a mask. After the transirradiation has been restarted, individual images are captured of the catheter inserted in the vessel that is to be examined, and these are superimposed on and subtracted from the stored mask image, so that an examiner can visually localize and place the catheter in the contrasted image by observing the superimposed total image.

The above-described road map technique requires that the instantaneous images of the catheter in the vessel be captured from the same exposure angle or projection angle of the X-ray device as the previously stored mask image, since otherwise these images can not be compared to the stored mask images, by being superimposed on them. As a result, in order to mark the individual vessels, it is necessary to make new contrast agent injections for each projection direction or for each exposure angle, so that difficult interventional procedures, such as those employed in the field of neuroradiology must be used. Since these procedures entail relatively frequent contrast agent injections, this makes rapid positioning and localizing of the catheter in the vessel to be examined difficult and prolongs the treatment period for the examination subject.

SUMMARY OF THE INVENTION

An object of the present invention is to provide a method for positioning a catheter which has been inserted into a vessel, as well as a corresponding device, which make it possible to position the catheter more rapidly and simply in the vessel which is to be examined and to avoid frequent contrast agent injections, in particular.

The basic idea of the aforementioned road map technique is also relied upon in the present invention for positioning the catheter in a vessel to be examined; that is, after a contrast agent has been injected, a contrast agent image is captured and stored as a mask of the respective vessel, the mask being superimposed by a subsequently captured single image of the vessel with inserted catheter, in order to be able to localize and place the catheter in the contrasted vessel using the thus-acquired total image. This is augmented in the present invention to achieve the above object by generating and storing a three-dimensional image of the vessel as the mask, this three-dimensional image being computed from a number of individual images that have been picked up from various projection angles or exposure angles with an X-ray device, by transirradiating the contrasted vessel. This procedure makes it possible to select that individual image of the three-dimensional mask image whose projection direction, or whose exposure angle, most optimally corresponds to the instantaneous exposure angle of the instantaneous image, depending on the projection direction of the subsequent instantaneous exposure of the examined vessel. This selected individual image is subsequently displayed with the individual instantaneous images superimposed thereon, in order to be able to localize and place the catheter visually in the contrasted vessel.

Using the invention, only a one-time contrast agent injection is required in order to generate a three-dimensional mask image. The individual images, which, when reconstructed, yield the three-dimensional mask image of the contrasted vessel, can be captured by rotating the pickup system of the X-ray device around the examination location. The invention thus guarantees that, despite a single one-time contrast agent injection, it is always possible to select the appropriate mask image and to superimpose the instantaneous images thereon, regardless of the actual projection direction used to capture the instantaneous images of the vessel to be examined, so that new injections of contrast agent are not required for each new positioning direction. Using the present invention, it is thus possible to rapidly and precisely localize and position the catheter in the vessel, so that the catheter can likewise be guided in the vessel rapidly and precisely to the desired target location, (the location of the examination).

The present invention also makes it possible, subsequent to capturing the three-dimensional mask image of the vessel, to select the projection direction or the exposure angle for capturing the instantaneous images which is optimal for catheter guidance, and to adjust the X-ray device accordingly. For this purpose, it is merely necessary to select the individual image of the three-dimensional mask image that corresponds to the projection direction that has been set, in order to be able to subsequently superimpose the instantaneous images thereon.

The present invention can be used either in a monoplanar transirradiation or in a biplanar transirradiation of the examination location, the instantaneous images being captured from only one projection direction or from two different projection directions, respectively. It can be guaranteed by appropriate matchings that the selected mask image is always displayed congruently to the captured instantaneous image, by employing the known pixel shifting technique for this purpose.

DESCRIPTION OF THE DRAWINGS

FIG. 1 is a simplified block diagram of a device for the angiographic examination of a subject in which the present invention is employed.

DESCRIPTION OF THE PREFERRED EMBODIMENTS

Figure 2A:
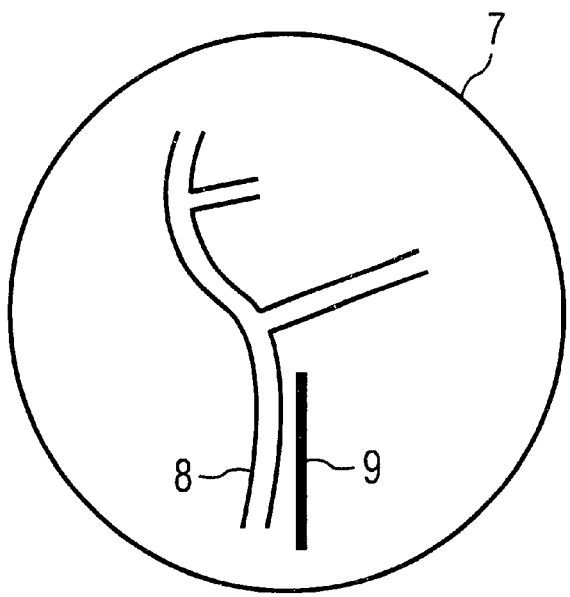
FIG. 2a and FIG. 2b illustrate a measure to make the mask image congruent to a captured instantaneous image.

The device illustrated in FIG. 1 is for angiographic examination of a subject 1, wherein fluoroscopic images are obtained of vessels of the subject 1 in order to be able to detect constrictions of the vessel or the like. The X-ray device includes a radiation source 2 (illustrated in FIG. 1) and an image capturing system 3, which includes an X-ray image amplifier and a monitor, in particular. The image capturing system 3 of this X-ray device is connected to an image processing unit 10, which evaluates or combines the fluoroscopic images captured by the X-ray device and displays them on a monitor 7. This allows an examiner to visually localize and place the catheter, which as been inserted into a vessel for purposes of angiographic examination, by observing the monitor 7, in order to be able to accurately follow branchings of the vessel and to guide the catheter continuously and precisely to the desired target location, for example.

The examination can proceed as follows:

First, a contrast agent is injected into the vessel in which the catheter is to be guided, in order to highlight the vessel path more sharply, and a mask image of the corresponding vessel is captured using the X-ray device, this being a matter of a three-dimensional image of the vessel. This three-dimensional mask image of the contrasted vessel is composed of a number of individual mask images which are captured by transirradiation of the vessel from different projection angles or exposure angles. This can ensue by rotating the radiation source 2 and the image capturing system 3, which are mounted on a C-arm, once around the corresponding body parts of the subject 1, with a number of individual mask images of the contrasted vessel being captured from different projection directions. The image data of these individual mask images are fed by the image capturing system 3 to a 3D mask image memory 4, which processes the image data and combines them into the three-dimensional mask image of the location of examination with the corresponding vessel; i.e., the 3D mask image memory 4 generates a three-dimensional image record which is obtained by combining the image data of the individual mask images that are captured from different projection directions. This three-dimensional image record is stored in the 3D mask image memory 4.

The above described procedure i s executed only once; that is, it is only necessary to perform a single injection of contrast agent into the vessel to be examined, i.e., into the corresponding examination location, in order to obtain the three-dimensional mask image.

The examiner subsequently selects the projection direction of the X-ray device which is optimal for catheter guidance and positions the radiation source 2 and the image capturing system 3 accordingly. The positioning of the X-ray device can occur either manually or automatically; that is, the examiner prescribes the desired projection direction to the device, and the radiation source 2 and the image capturing system 3 are positioned by a suitable drive corresponding to the desired projection direction, in order to be able to subsequently execute the instantaneous exposures, required for the road map technique, of the corresponding vessel.

Next, dependent on the selected direction of projection, the image data of that individual mask image whose projection direction corresponds to the selected direction is selected from the three-dimensional image record of the 3D mask image memory 4. If this is not possible, that individual mask image is selected whose projection direction most optimally corresponds to the direction of projection of the X-ray device that has been set. The selection of the image data of the individual mask image to be selected can ensue manually. An automatic selection, however, is preferable; that is, depending on the desired direction of projection, the 3D mask image memory 4 may have processing capability allowing it to automatically select the image data of that individual mask image, from the three-dimensional image record of the previously obtained three-dimensional mask image of the contrasted vessel, whose projection direction best corresponds to the desired projection direction. However selected, the data for this image are supplied to an image processor 6, which superimpose the individual mask image on the subsequently captured instantaneous images of the vessel (examination location), and to displays these latter images on the monitor 7.

The corresponding body part of the subject 1 is subsequently transirradiated again, and an instantaneous image of the vessel is captured with the catheter inserted, which image is fed to an image memory, which may also have computing capability 5. This image memory 5 processes the image data of the instantaneous image which is captured from the previously set projection direction and feeds the image data to the image processor 6, so that the processor 6 can superimpose the previously selected individual mask image of the three-dimensional mask image, which is supplied from the 3D mask image memory 4, on the image data of the instantaneous image and can display this resulting image data on the monitor 7. The processor 6 thus always superimposes an individual mask image, which is previously selected corresponding to the desired projection direction, of the three-dimensional mask image of the contrasted vessel, on an instantaneously captured individual image. By using the monitor 7, an examiner can thus localize and place the catheter in the contrasted vessel.

The device illustrated in FIG. 1 is for angiographic examination of the subject 1, wherein a monoplanar transirradiation is performed; that is, an instantaneous exposure of the respective vessel always occurs from one previously set projection direction. The present invention can be applied just as well for biplanar transirradiation, in which instantaneous exposures are performed from two different directions of projection. To this end, the device illustrated in FIG. 1 is expanded by an additional image memory 5 along with an additional processor 6, the instantaneous image of the desired examination location from a different projection direction being fed to this additional image memory 5. In this case, the additional processor 6 receives the corresponding image data of the additional image memory 5 and would access the shared 3D mask image memory 4 in order to select that individual mask image of the previously obtained three-dimensional mask image which corresponds optimally to the projection direction, and to superimpose the individual mask image thereon. In this way, a second superimposed total image of the examination location of the subject 1 is generated, which may be displayed on a separate monitor or together with the previously described first superimposed total image on the same monitor 7, so that the examiner can observe the catheter guidance in the vessel from different viewing angles.

The captured instantaneous image, which is stored in the image memory 5, is distorted to a certain extent by the X-ray image amplifier contained in the image capturing system 3.

In order to be able to compare this instantaneous image to the corresponding individual mask image, and to be able to superimpose this mask image thereon despite this distortion, it is necessary either to correct the distortion of the instantaneous image according to the X-ray image amplifier distortion or to correspondingly distort the selected individual image mask of the 3D mask image memory 4 according to the X-ray image amplifier distortion, so that equally corrected or equally distorted individual images are superimposed by the processor 6 and displayed on the monitor 7. Correction of the distortion of the instantaneous image, or the distortion of the individual mask image, can be performed by appropriate image processing software in the processor 6.

When the instantaneous image of the image memory 5 is superimposed with the selected individual mask image from the 3D mask image memory 4, the image background, i.e. bones and the like, can still be seen on the monitor 7. In order to be able to display only the catheter with the individual mask image of the three-dimensional mask image of the 3D mask image memory 4 on the display 7, it is possible to execute an additional instantaneous image capture of the examination location without contrast agent injection and without a catheter, that is, given a withdrawn catheter, prior to the actual transirradiation with the previously set projection direction of the X-ray device, the corresponding image data for this image also being stored in the image memory 5, for example. The image memory 5 then subtracts the image data forming this "empty" image from the image data of the instantaneous images that are obtained subsequently by transirradiation with the catheter present, and supplies the image data representing this revised image to the processor 6. The processor 6 superimposes the individual mask image, supplied by the 3D mask image memory 4, of the three-dimensional mask image on this revised instantaneous image, or subtracts the individual mask image therefrom, in order to display a corresponding total image on the monitor 7. Alternatively, it is also possible to generate a series of empty images which are subtracted from the respective instantaneous images acquired during transirradiation with the catheter present, so that the three-dimensional mask image is acquired as a series of subtraction images produced by the subtraction of an instantaneous image, which is captured during transirradiation, from a corresponding empty image.

The X-ray device can have certain mechanical device tolerances which may lead to imprecisions in the image capture and consequently in the positioning of the catheter. To this end, prior to the actual initial operation of the X-ray device, a test run of the C-arm with the radiation source 2 and the image capturing system 3 can be conducted, with a calibrating phantom disposed in the examination field of view and with image data from the phantom being detected during the trial, in order to subsequently have the ability to calculate the device tolerances or device deviations and to take these into account in the image processing of the captured images. Only the device tolerances for the specified motion plane of the C-arm of the X-ray device, however, can be computed and taken into account by means of this calibration run. A calibration run for every arbitrary device position, which would amount to a complete three-dimensional calibration, cannot be performed for reasons of outlay and complexity. Nevertheless, when another base positional setting of the device is selected for transirradiating the subject 1, it is still possible, as described above, to select, from the three-dimensional image record of the 3D mask image memory 4, that individual mask image whose image projection direction best corresponds to the instantaneous projection direction. Due to the device tolerances, however, which are not calibrated for this device position, there are convergence errors between the selected individual mask image and the instantaneous image which is captured in the set direction of projection and which is stored in the image memory 5. A postprocessing of the images thus is necessary, in order to make the instantaneous image congruent to the individual mask image. This postprocessing can be executed automatically or semiautomatically by the processor 6 in the form of a two-dimensional or three-dimensional matching, whereby preferably either the image structures used for this are the same in the selected individual mask image of the three-dimensional mask picture of the 3D mask image memory 4 and in the instantaneous image of the image memory 5, or there must necessarily be a correlation between them. This is described in detail below.

For example, it is possible to bring the instantaneous image into congruence with the selected individual mask image of the three-dimensional mask image by bringing the individual pixels into congruence by x and y shifting. This method is termed pixel shifting and can be performed automatically by the processor 6, for example. In a biplanar exposure, the matching or aligning between the two instantaneous images of the different projection directions and a corresponding individual image mask of the three-dimensional mask picture can ensue in succession or in alternation in a three-dimensionally interactive manner; i.e., the two instantaneous images of the examination location, which are captured from different projection directions, are brought into congruence with the correspondingly selected individual mask image of the previously captured and stored three-dimensional mask image separately from one another.

Figure 2B:
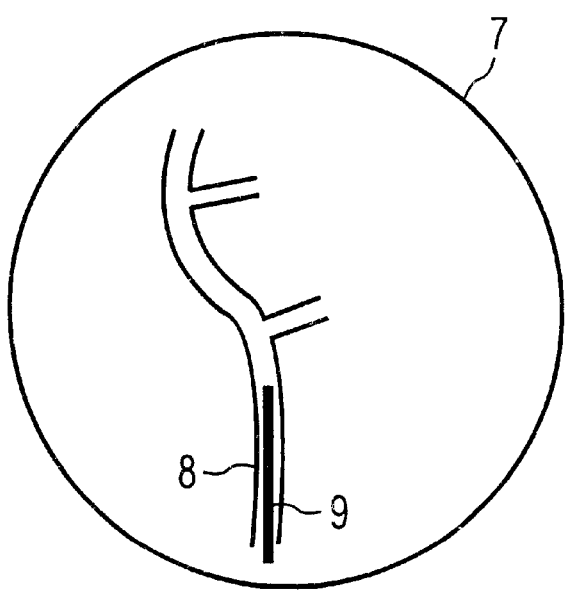

When the catheter is already situated in the vicinity of the target region or the desired examination location, a direct matching is performed for the catheter with the vessel representations of the mask image of the three-dimensional mask picture. The fact that the catheter must be located in the corresponding vessel is exploited for this purpose. FIG. 2a illustrates the display on the monitor 7 for the case when the representation of a vessel 8 which is obtained by means of a selected individual mask image of the three-dimensional mask image of the 3D mask image memory 4 is not congruent to the representation of the catheter 9, this representation having been obtained by means of the instantaneous pickup with the image memory 5. Since it is necessary for the catheter 9 to be situated in the vessel 8, the individual mask image of the three-dimensional mask image, or alternatively the instantaneous exposure image of the transillumination, can be shifted such that the catheter 9 comes to be situated in the vessel 8, as is illustrated in FIG. 2b.

If the catheter is already situated in the vicinity of the target region, another alternative is to perform a trial injection of the contrast agent during transirradiation and the captured and stored individual image of the vessel obtained as a result can be brought into congruence with the identical vessels of the previously captured mask image of the three-dimensional mask image, in order to guarantee that the instantaneous image of the image memory 5 that is captured in the corresponding device position is congruent to the individual mask image of the three-dimensional mask image of the 3D mask image memory 4.

The above-described matching measures cause the instantaneous image of the examination location, i.e., of the corresponding vessel, obtained during transirradiation, to be brought exactly into congruence with the previously captured vessel image of the three-dimensional mask image, so that the inventively executed road map technique leads to the result of a reliable and certain localization and placement of the catheter in the corresponding vessel.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for in vivo positioning of a catheter relative to a vessel, comprising the steps of:
    (a) injecting a contrast agent into a vessel and generating a three-dimensional image of the vessel with the contrast agent by irradiating an examination region containing said vessel from a plurality of different exposure directions and obtaining a plurality of first individual images of the vessel respectively from the exposure directions without stereotactic instrument, and combining said first individual images to form said three-dimensional image;
    (b) obtaining a second individual image of said examination region containing said vessel, with a catheter inserted in said vessel, by irradiating said examination region from a selected exposure direction initially uncorrelated with any of said first images;
    (c) selecting one of said first individual images in said plurality of first individual images forming said three-dimensional image, obtained at an exposure direction which corresponds most closely to said exposure direction of said second individual image; and
    (d) combining said one of said first individual images selected in step (c) with said second individual image obtained in step (b) to form a combination image of said vessel with said catheter inserted therein, said combination image showing a position of the catheter in the vessel, and displaying said combination image.

2. A method as claimed in claim 1 wherein each of said first individual images in said plurality of first individual images obtained in step (a) is comprised of image data, and wherein step (a) includes compiling an image data record, corresponding to said three-dimensional image, of all of the image data respectively forming said plurality of first individual images, and wherein said second individual image obtained in step (b) is comprised of image data, and wherein step (c) comprises selecting image data from said image data record corresponding to said one of said first individual images, and wherein step (d) comprises combining the image data comprising said second individual image with the image data comprising said one of said first individual images selected in step (c).

3. A method as claimed in claim 1 wherein the step of obtaining said plurality of first individual images comprises irradiating said examination region with an X-ray device having a radiation source and a radiation detector disposed on opposite sides of said examination region by rotating said X-ray device around said exposure region through said plurality of exposure directions.

4. A method as claimed in claim 1 wherein step (b) comprises selecting said selected exposure direction to be suitable for guiding said catheter in said vessel.

5. A method as claimed in claim 1 wherein step (b) comprises obtaining said second individual image with an X-ray device having a distortion characteristic associated therewith which causes said second individual image to be distorted, and wherein step (b) further comprises correcting said second individual image dependent on said distortion characteristic to obtain an undistorted second individual image and using said undistorted second individual image to form said combined image.

6. A method as claimed in claim 1 wherein step (b) comprises obtaining said second individual image with an X-ray device having a distortion characteristic associated therewith, so that said second individual image is a distorted second individual image, and wherein step (c) comprises distorting said one of said first individual images which is selected, dependent on said distortion characteristic, to obtain a distorted first individual image which is distorted comparably to said distorted second individual image, and using said distorted first individual image and said distorted second individual image in step (d) to form said combined image.

7. A method as claimed in claim 1 comprising the additional step, before step (b), of obtaining a third individual image of said examination region containing said vessel, without said catheter therein, from said selected exposure direction of step (b), and wherein step (b) comprises subtracting said third individual image from said second individual image to obtain a subtraction image, and wherein step (d) comprises combining said subtraction image, as said second individual image, with said first individual image to form said combination image.

8. A method as claimed in claim 1 wherein step (a) comprises obtaining said plurality of first individual images with an X-ray device and wherein step (b) comprises obtaining said second individual image with said X-ray device, and comprising the additional step, preceding step (a), of conducting a test run of said X-ray device with a calibration phantom, and obtaining a test image, said test image containing a representation of any mechanical tolerances of said X-ray device, and comprising the additional step of correcting at least one of said one of said first individual images selected in step (c), said second individual image obtained in step (b), and said combination image obtained in step (d) to correct for said mechanical tolerances using said test image.

9. A method as claimed in claim 1 wherein step (d) further comprises conducting an image matching procedure for substantially eliminating any convergence errors between the first individual image selected in step (c) and said second individual image obtained in step (b).

10. A method as claimed in claim 9 wherein said image matching procedure comprises conducting automatic pixel shifting between said first individual image selected in step (c) and said second individual image obtained in step (b).

11. A method as claimed in claim 9 wherein said image matching procedure comprises shifting said first individual image selected in step (c) and said second individual image obtained in step (b) relative to each other so that said catheter comes to be situated in said vessel in said combination image.

12. A method as claimed in claim 8 wherein said image matching procedure comprises, after injecting said contrast agent, obtaining an additional individual image of said vessel from the selected exposure direction of step (b), and shifting said second individual image obtained in step (b) and said first individual image selected in step (c) relative to each other so that a representation of said vessel in said first individual image selected in step (c) is congruent to a representation of said vessel in said additional individual image.

13. A method as claimed in claim 1 comprising the additional steps of:

obtaining an additional second individual image of said examination region containing said vessel, with said catheter inserted in said vessel, by irradiating said examination region from an additional selected exposure direction;

selecting an additional one of said first individual images in said plurality of first individual images, forming said three-dimensional image, obtained at an exposure direction which corresponds most closely to said additional exposure direction of said additional second individual image; and combining said additional one of said first individual images with said additional second individual image to form an additional combination image of said vessel with said catheter inserted therein, said additional combination image showing a position of the catheter in the vessel viewed from a different direction from said combination image, and displaying said additional combination image together with said combination image.

14. An apparatus for in vivo positioning of a catheter relative to a vessel, comprising:

a non-stereotactic radiological exposure device for irradiating an examination region, containing a vessel with a contrast agent injected therein, from a plurality of different exposure directions for obtaining a plurality of first individual images of the vessel from the respective exposure directions;

a first memory for storing said first individual images and for combining said first individual images to form a three-dimensional image;

said radiological exposure device obtaining a second individual image of said examination region containing said vessel, with a catheter inserted in said vessel, by irradiating said examination region from a selected exposure direction initially uncorrelated with any of said first images;

a second memory for storing said second individual image;

an image processor connected to said first and second memories for selecting one of said first individual images forming said three-dimensional image from said first memory which was obtained at an exposure direction which corresponds most closely to said exposure direction of said second individual image, and for combining said one of said first individual images with said second individual image from second memory to form a combination image of said vessel with said catheter inserted therein, said combination image showing a position of the catheter in the vessel; and a monitor connected to said image processor for displaying said combination image.

15. An apparatus as claimed in claim 14 wherein said radiological exposure device comprises an X-ray device having a radiation source and a radiation detector disposed on opposite sides of said examination region, said X-ray device being rotatable around said exposure region through said plurality of exposure directions.

16. An apparatus as claimed in claim 15 wherein said X-ray device has a distortion characteristic associated therewith which causes said second individual image to be distorted, and further comprising means for correcting said second individual image dependent on said distortion characteristic to obtain an undistorted second individual image and wherein said image processor uses said undistorted second individual image together with said one of said first individual images to form said combined image.

17. An apparatus as claimed in claim 15 wherein said X-ray device has a distortion characteristic associated therewith, so that said second individual image is a distorted second individual image, and further comprising means for distorting said one of said first individual images, dependent on said distortion characteristic, to obtain a distorted first individual image which is distorted comparably to said distorted second individual image, and wherein said image processor uses said distorted first individual image and said distorted second individual image to form said combined image.

18. An apparatus as claimed in claim 14 wherein said image processor conducts an image matching procedure for substantially eliminating any convergence errors between said one of said first individual images and said second individual image.

19. An apparatus as claimed in claim 18 wherein said image processor conducts automatic pixel shifting between said one of said first individual images and said second individual image as said image matching procedure.

20. An apparatus as claimed in claim 14 wherein said radiological exposure device obtains a second individual image of said examination region containing said vessel, with said catheter inserted in said vessel, by irradiating said examination region from an additional selected exposure direction, and wherein said apparatus comprises an additional image processor for selecting an additional one of said first individual images forming said three-dimensional image which was obtained at an exposure direction which corresponds most closely to said additional exposure direction of said additional second individual image, and for combining said additional one of said first individual images with said additional second individual image to form an additional combination image of said vessel with said catheter inserted therein, said additional combination image showing a position of the catheter in the vessel viewed from a different direction from said combination image, and wherein said monitor displays said combination image and said additional combination image.

* * * * *